United States Patent
Cardoso, Jr. et al.

(10) Patent No.: US 9,079,059 B2
(45) Date of Patent: Jul. 14, 2015

(54) SYSTEM AND METHOD FOR GENERATING AND USING CUSTOMIZED ATHLETIC WORKOUTS

(71) Applicant: Pioneer Advanced Solutions, Inc., San Jose, CA (US)

(72) Inventors: Augusto C. Cardoso, Jr., Oakland, CA (US); Robert Curtis Cole, Los Altos, CA (US); Victor Chernetsky, Cupertino, CA (US); Jerry Dunmire, Santa Clara, CA (US); Charles Paul Morel, San Jose, CA (US); Dan Phan, San Jose, CA (US)

(73) Assignee: Pioneer Advanced Solutions, Inc., San Jose, CA (US)

( * ) Notice: Subject to any disclaimer, the term of this patent is extended or adjusted under 35 U.S.C. 154(b) by 84 days.

(21) Appl. No.: 13/852,045

(22) Filed: Mar. 28, 2013

(65) Prior Publication Data

US 2013/0261776 A1     Oct. 3, 2013

Related U.S. Application Data

(60) Provisional application No. 61/616,642, filed on Mar. 28, 2012.

(51) Int. Cl.
| | |
|---|---|
| *G06F 17/00* | (2006.01) |
| *A63B 24/00* | (2006.01) |
| *G06F 19/00* | (2011.01) |
| *G01S 19/19* | (2010.01) |

(52) U.S. Cl.
CPC ........ *A63B 24/0062* (2013.01); *G06F 19/3481* (2013.01); *G01S 19/19* (2013.01)

(58) Field of Classification Search
CPC ..................................................... A63B 24/062
USPC ........................................ 700/90, 91, 94, 108
See application file for complete search history.

(56) References Cited

U.S. PATENT DOCUMENTS

| | | |
|---|---|---|
| 6,626,799 B2 | 9/2003 | Watterson et al. |
| 7,254,516 B2 | 8/2007 | Case, Jr. et al. |
| 7,292,867 B2 | 11/2007 | Werner et al. |
| 7,603,255 B2 | 10/2009 | Case, Jr. et al. |
| 7,643,895 B2 | 1/2010 | Gupta et al. |
| 7,771,320 B2 | 8/2010 | Riley et al. |

(Continued)

FOREIGN PATENT DOCUMENTS

| | | |
|---|---|---|
| KR | 20100118783 | 11/2010 |
| WO | 2012021507 | 2/2012 |

OTHER PUBLICATIONS

International Search Report and Written Opinion dated Jul. 11, 2013 of International Application No. PCT/US2013/034254.

(Continued)

*Primary Examiner* — Ronald Laneau
(74) *Attorney, Agent, or Firm* — David D. Brush; Westman, Champlin & Koehler, P.A.

(57) ABSTRACT

A method for generating and using a workout file, comprising recording workout data and notes while performing an athletic workout, attaching trigger conditions to the notes, and exporting the workout data, the notes, and the attached trigger conditions as the workout file, where the exported workout file is configured to be used by a subsequent user to repeat the athletic workout in a manner that plays the notes when the subsequent user performs the trigger conditions.

20 Claims, 8 Drawing Sheets

(56) References Cited

U.S. PATENT DOCUMENTS

| | | |
|---|---|---|
| 7,815,548 B2 | 10/2010 | Barre et al. |
| 7,841,967 B1 | 11/2010 | Kahn et al. |
| 7,860,583 B2 | 12/2010 | Condurso et al. |
| 7,887,329 B2 | 2/2011 | Greenshpan et al. |
| 7,952,483 B2 | 5/2011 | Ferguson et al. |
| 7,959,567 B2 | 6/2011 | Stivoric et al. |
| 8,005,691 B2 | 8/2011 | Kumar et al. |
| 8,033,959 B2 | 10/2011 | Oleson et al. |
| 2006/0099556 A1* | 5/2006 | Yeo et al. .................. 434/247 |
| 2009/0047645 A1* | 2/2009 | Dibenedetto et al. ....... 434/258 |
| 2009/0048070 A1* | 2/2009 | Vincent et al. .................. 482/8 |
| 2010/0210421 A1 | 8/2010 | Case, Jr. et al. |
| 2011/0098928 A1* | 4/2011 | Hoffman et al. ................ 702/5 |
| 2011/0196603 A1 | 8/2011 | Graham et al. |
| 2011/0201476 A1 | 8/2011 | Solomon |
| 2011/0221670 A1 | 9/2011 | King, III et al. |
| 2011/0221671 A1 | 9/2011 | King, III et al. |
| 2011/0227813 A1 | 9/2011 | Haddick et al. |
| 2011/0275480 A1 | 11/2011 | Champsaur |
| 2011/0288379 A1 | 11/2011 | Wu |
| 2012/0015778 A1 | 1/2012 | Lee et al. |
| 2013/0135115 A1* | 5/2013 | Johnson et al. ........... 340/870.02 |
| 2013/0238287 A1* | 9/2013 | Hoffman et al. .............. 702/189 |

OTHER PUBLICATIONS

"GPS Course Creator", GPSCC Manual, Jun. 2006.
www.computrainer.com, "Products—GPS Course Creator", Datasheet, publicly published prior to Dec. 27, 2011.
www.racermateinc.com, "Coaching Software", Dec. 27, 2011.
www.racermateinc.com, "TOPO USA—3D Course Creation Software", Dec. 27, 2011.

\* cited by examiner

SYSTEM AND METHOD FOR GENERATING AND USING CUSTOMIZED ATHLETIC WORKOUTS

CROSS-REFERENCE TO RELATED APPLICATION(S)

This application claims priority to U.S. Provisional Patent Application No. 61/616,642, filed on Mar. 28, 2012, and entitled "SYSTEM AND METHOD FOR GENERATING AND USING CUSTOMIZED ATHLETIC WORKOUTS".

FIELD

The present disclosure is directed to athletic performance methods and devices. In particular, the present disclosure is directed to methods for generating customized athletic workouts for use with electronic devices.

BACKGROUND

Athletic workouts are commonly performed to enhance or maintain physical fitness and health, and for purposes of personal achievements. Over the past several decades, a growing number of people have dedicated significant efforts to athletics and physical fitness. This is due in part to the heightened awareness of the health benefits attained from good physical fitness. Furthermore, the increased popularity of athletic events, such as running, cycling, and triathlons, have driven people to further improve their fitness levels.

Many people participating in physical fitness activities, particularly athletes, have accepted the use of health monitoring devices, such as heart rate monitors, in their training routines. Such devices improve training efficiencies, thereby increasing overall athletic fitness. With the increased use of wireless technologies, the number of health monitoring devices commercially available to the general public has also grown.

Another common practice for serious athletes, including professional and age group athletes, is to hire coaches who provide guidance and education during the athletes' training. Coaches have likewise styled their workout plans for athletes to incorporate health monitoring devices. However, generating workouts that are useful, motivating, and that incorporate health monitoring devices can require substantial time commitments by the coaches. As such, there is a need for techniques to generate effective athletic workouts that incorporate health monitoring, and that also reduce the time commitments by coaches and other instructors.

SUMMARY

An aspect of the present disclosure is directed to a method for generating a workout file. The method includes performing an athletic workout, recording workout data while performing the athletic workout (e.g., route information of the athletic workout, biometric parameters, and/or environment information during the athletic workout). The method also includes recording notes while performing the athletic workout, where the recorded notes are linked to the recorded workout data, and storing the recorded workout data and the recorded notes on a computer readable medium. The method further includes attaching trigger conditions to the stored notes, and exporting the stored workout data, the stored notes, and the attached trigger conditions as the workout file, where the exported workout file is configured to be used by a subsequent user to repeat the athletic workout in a manner that plays the notes when the subsequent user performs the trigger conditions.

Another aspect of the present disclosure is directed to a method for generating a workout file, which includes performing an athletic workout along a route, recording GPS coordinate waypoints along the route while performing the athletic workout with a GPS receiver, and recording notes while performing the athletic workout along the route, where the notes are time-stamp linked to the recorded GPS coordinate waypoints corresponding to when the notes are recorded. The method also includes attaching trigger conditions to the recorded notes, where at least a portion of the attached trigger conditions are based on GPS coordinate waypoints, and exporting the GPS coordinate waypoints, the recorded notes, and the attached trigger conditions as the workout file.

Another aspect of the present disclosure is directed to a workout device assembly that includes one or more sensors configured to read workout data while a first person performs an athletic workout, where the workout data includes route information of the athletic workout, biometric parameters of the first person, and/or environment information during the athletic workout. The assembly also includes one or more note inputs configured to receive notes from the first person while the first person performs the athletic workout, and a first device transportable by the first person and configured to record the workout data from the one or more sensors and the notes from the one or more note inputs, and to transmit the recorded workout data and the recorded notes. The assembly also includes a computer readable medium retaining programmable instructions that, when executed with a computer processor, enable trigger conditions to be attached the recorded notes, and exportation of the recorded workout data, the recorded notes, and the attached trigger conditions as a workout file.

DETAILED DESCRIPTION

The present disclosure is directed to a first method for authoring or otherwise generating customized athletic workouts (referred to as an "authoring method"), to a second method for using the customized athletic workouts (referred to as a "playback method"), and to devices configured to generate and use the customized athletic workouts. As discussed below, the authoring method is suitable for generating workout files in a convenient and efficient manner. The generated workout files provide virtual or real-life instructor experiences for subsequent users under the playback method.

For ease of discussion, the authoring method will be described as being performed by an "instructor", and the playback method will be described as being performed by an "athlete". However, the authoring and playback methods may each be performed and used by any suitable person or persons. For example, the instructor may be a training coach, a professional or otherwise experienced athlete, an exercise instructor, a personal trainer, and the like. Correspondingly, the athlete may be a sports athlete, a person who desires to exercise (e.g., for weight loss), a person undergoing physical therapy, and the like.

Figure 1:
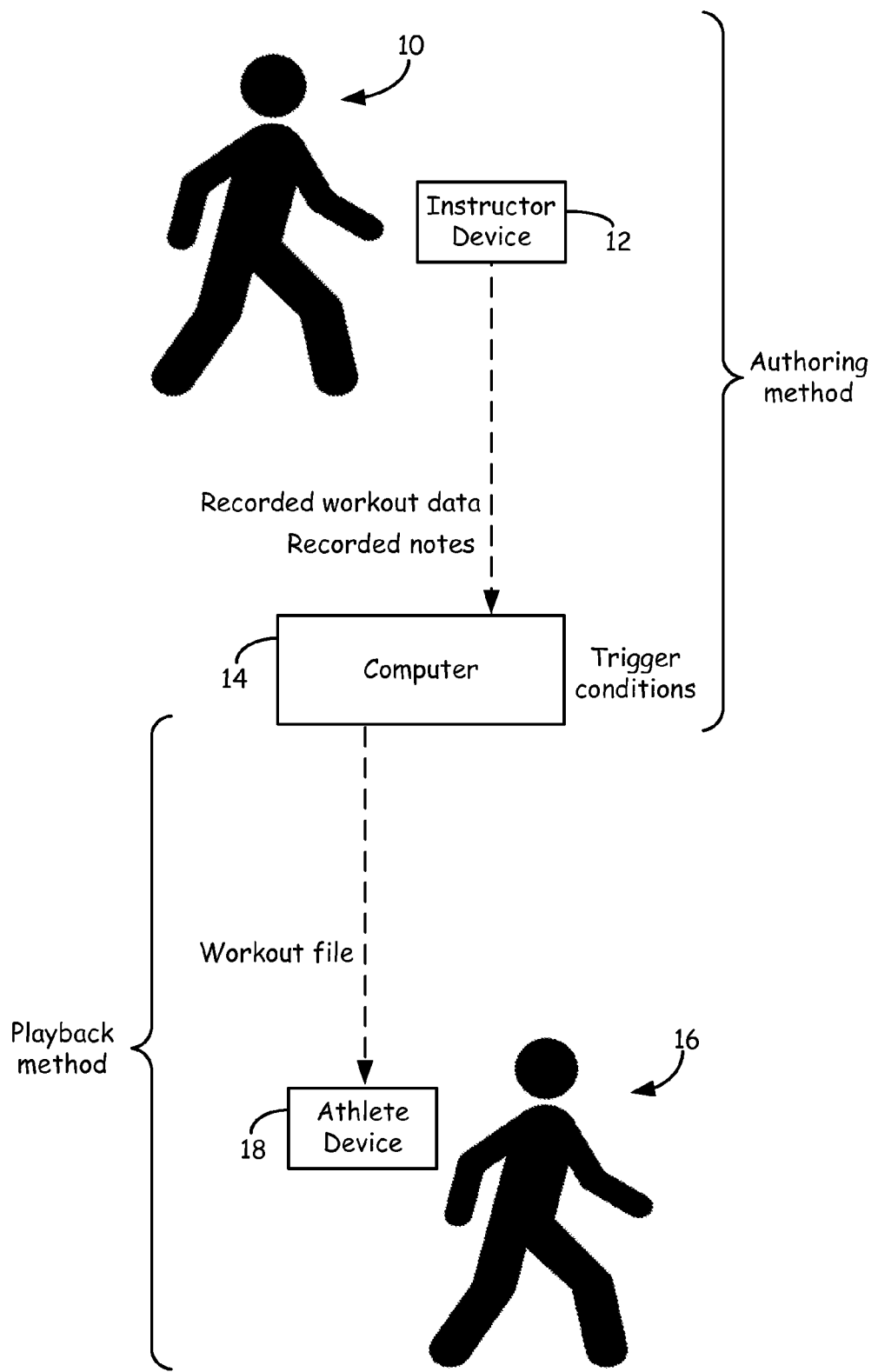
FIG. 1 is an illustration of a first person performing an authoring method of the present disclosure, and of a second person performing a playback method of the present disclosure.

FIG. 1 illustrates an example of the authoring and playback methods. Briefly, under the authoring method, instructor 10 generates a customized athletic workout by performing personally an athletic workout, and recording his or her workout data with instructor device 12. As used herein, the terms "workout" and "athletic workout" each refer to any session of exercise or practice to improve physical performance, and includes, for example, training and physical fitness workouts, athletic competition and time trial events, physical fitness tests, aerobic routines, and the like.

During the athletic workout, instructor 10 may also record notes (e.g., audio, video, and textual notes) with instructor device 12, which are time stamped and/or location stamped to the recorded workout data. Instructor 10 then attaches trigger conditions to these recorded notes with computer 14, and exports the resulting data as a digital file of the customized athletic workout, referred to as a "workout file". As also shown, under the playback method, athlete 16 may then import the workout file to athlete device 18 for use in a subsequent athletic workout by athlete 16.

Figure 2:
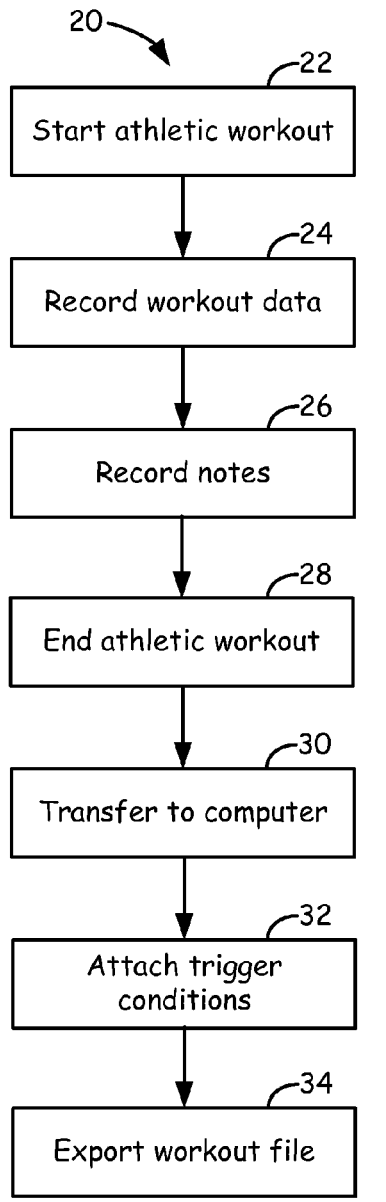
FIG. 2 is a flow diagram of example steps for the authoring method.
Figure 3:
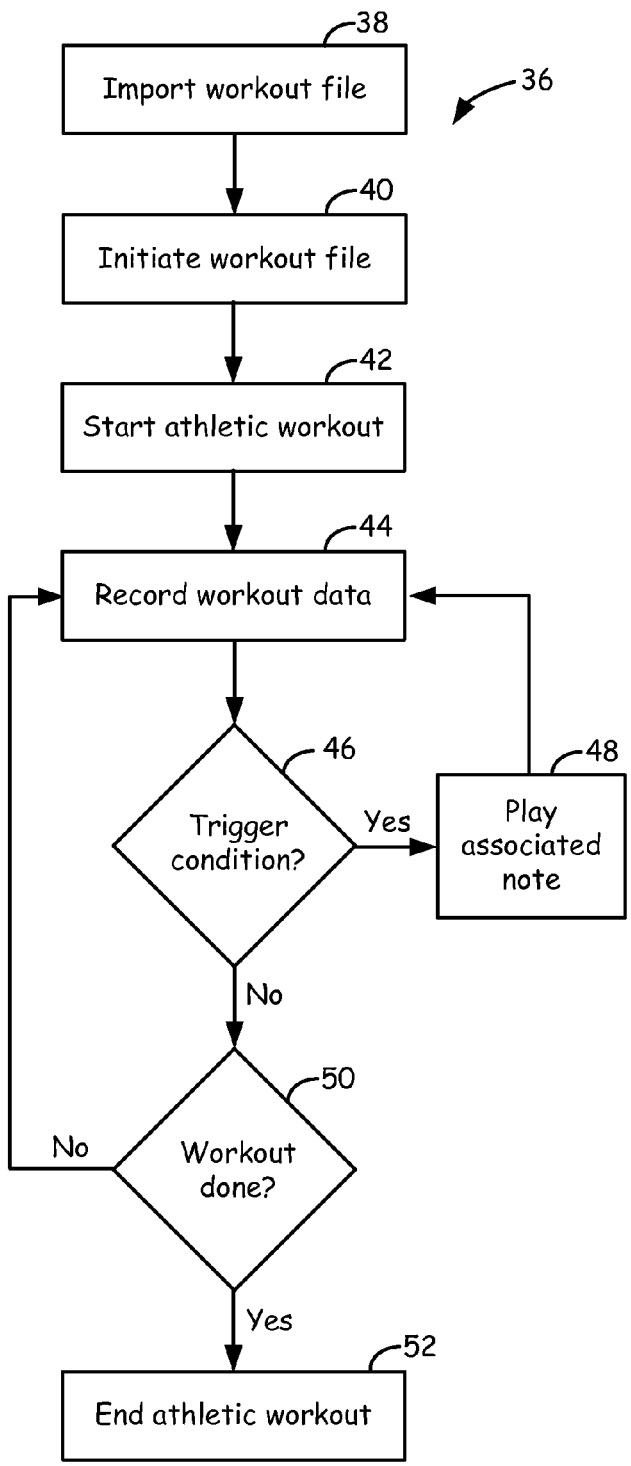
FIG. 3 is a flow diagram of example steps for the playback method.

FIGS. 2 and 3 respectively illustrate example steps for the authoring method and the playback method. As shown in FIG. 2, authoring method 20 includes steps 22-34, and initially involves having instructor 10 start an athletic workout while using instructor device 12 (step 22). Instructor device 12 is a first electronic device that may be wearable or otherwise retained by instructor 10 during the athletic workout, such as a wrist-wearable device or a cycling computer. While instructor 10 performs the athletic workout, instructor device 12 records his or her workout data (step 24). The recorded workout data for instructor 10 may include, for example, route information of the athletic workout (e.g., GPS waypoint coordinates, elevation, speed, and the like), biometric parameters of instructor 10 (e.g., heart rate, power output, cadence, core temperature, and the like), and/or environment information during the athletic workout (e.g., temperature, humidity, wind speeds, and the like).

Also while performing the athletic workout, instructor 10 may record notes, which are time stamped and/or location stamped to the recorded workout data (step 26). The recorded notes may provide a variety of different information, such as coaching advice and motivation during particular points of the athletic workout. After the athletic workout is complete (step 28), instructor 10 may transfer the recorded workout data and the recorded notes from instructor device 12 to computer 14 (step 30).

Computer 14 may be any suitable computer-based system (e.g., a personal computer, laptop computer, server-based system, mobile device, computer tablet device, and the like). Briefly, computer 14 is configured to communicate with instructor device 12 and athlete device 18, and to allow instructor 10 or any other suitable person to attach trigger conditions to the recorded notes (step 32). As discussed below, the trigger conditions dictate when the recorded notes are played or otherwise presented to athlete 16. In some embodiments, instructor 10 may optionally modify any desired portions of the recorded workout data and/or notes. For example, instructor 10 may modify the time-stamped locations of one or more of the notes. Instructor 10 may then export the recorded workout data, the recorded workout notes, and the trigger conditions as a workout file, which may be stored on computer 14 or other computer-based system for subsequent use by athlete 16 (step 34).

As shown in FIG. 3, playback method 36 includes steps 38-52, and initially involves importing the workout file to athlete device 18 (step 38). Athlete device 18 is a second electronic device that may be wearable or otherwise retained by athlete 16 during the workout, such as a wrist-wearable device or cycling computer. In some embodiments, instructor device 12 and athlete device 18 may be identical devices, allowing the same type of device to be used for both authoring method 20 and playback method 36. In other embodiments, athlete device 18 may be a computer-controlled exercise system (e.g., an indoor training system) configured to operate with the workout files.

After importing the workout file, athlete 16 may start the imported workout file (step 40) and perform an athletic workout with athlete device 18 that corresponds to the imported workout file (step 42). In other words, athlete 16 may perform a second athletic workout that corresponds to the above-discussed first athletic workout previously performed by instructor 10. While athlete 16 performs the athletic workout, athlete device 18 records his or her workout data, such as route information of the athletic workout, biometric parameters of athlete 16, and/or environment information during the workout for athlete 16 (step 44). When athlete 16 reaches one or more of the trigger conditions (step 46), the related notes are then played to athlete 16.

For example, an attached trigger condition may be reached when athlete 16 reaches a particular route location, when the heart rate of athlete 16 exceeds a defined rate, when the ambient temperature exceeds a defined temperature value, and the like. The trigger conditions may also be based on combinations of the route information, biometric parameters, and/or environment information, as defined by instructor 10 in step 32 of authoring method 20 (shown in FIG. 2).

While athlete 16 performs the athletic workout (step 50), athlete device 18 may continue to record the workout data for athlete 16 (step 44) and check whether any trigger conditions are reached (step 46). For trigger conditions based on successive GPS waypoint coordinates along a route, the recorded notes are typically played in a consecutive manner as athlete 16 moves along the route. In comparison, for trigger conditions based on biometric parameters, speed, and environmental information, the recorded notes associated with these trigger conditions may be performed in different orders depending on which trigger conditions are reached.

Furthermore, trigger conditions based on combinations of route information, biometric parameters, and/or environmental information may also be performed in a variety of different orders depending on which trigger conditions are reached. When the workout is complete (step 52), athlete 16 may close the workout file in athlete device 18, and optionally save or otherwise transfer his or her workout information to another computer-based system for safe keeping and analysis.

As can be appreciated, authoring method 20 (shown in FIG. 2) is suitable for generating workout files in a convenient and efficient manner. This can reduce the time and effort required by instructor 10 to generate workouts for athletes. Furthermore, by actually performing the athletic workout, instructor 10 may obtain a better understanding and appreciation of the factors that may occur when athlete 16 subsequently performs the athletic workout. This can provide a virtual or real-life instructor experience for athlete 16 while athlete 16 performs the athletic workout under playback method 36.

The workout file generated pursuant to authoring method 20 may be generated and made available for a variety of different uses. In some embodiments, authoring method 20 may be used to generate commercially available workout files that may be purchased and downloaded by consumers for a variety of workout plans.

In one example, instructor 10 may be a professional or otherwise experienced athlete who records workout data and notes during an athletic event with instructor device 12, such as while performing a training workout, an athletic competition, a time trial event, and the like. In this example, the recorded workout data may include route information (e.g., the GPS waypoint locations, elevation, and speed or pace) and the professional athlete's biometric parameters (e.g., heart rate, power output, cadence, and the like). The recorded workout data may also optionally include environment information (e.g., temperature, humidity, wind speed, and the like).

During the athletic workout, the professional athlete may also record audio and/or video notes for subsequent playback. After the workout is completed, the professional athlete (or other suitable person) may transfer the recorded workout data and notes to a computer-based system (e.g., computer 14), attach trigger conditions to the recorded notes, and export the resulting data as a workout file. This exported workout file may then be made available for purchase and download, such as by an e-commerce transaction over the Internet.

Under playback method 36, subsequent athletes may then purchase, download, and use the workout file during their training workouts. During these workouts, the recorded notes, such as motivational notes to push the athletes to keep up with the pace or intensity of the professional athlete, may be played when the attached trigger conditions are met. This can provide a virtual experience of training or racing with the professional athlete. Furthermore, during or after these workouts, the athletes may compare their route information, biometric parameters, and/or environment information to those of the professional athlete to identify their relative levels of fitness, areas of strengths and weaknesses, and the like.

Figure 4:
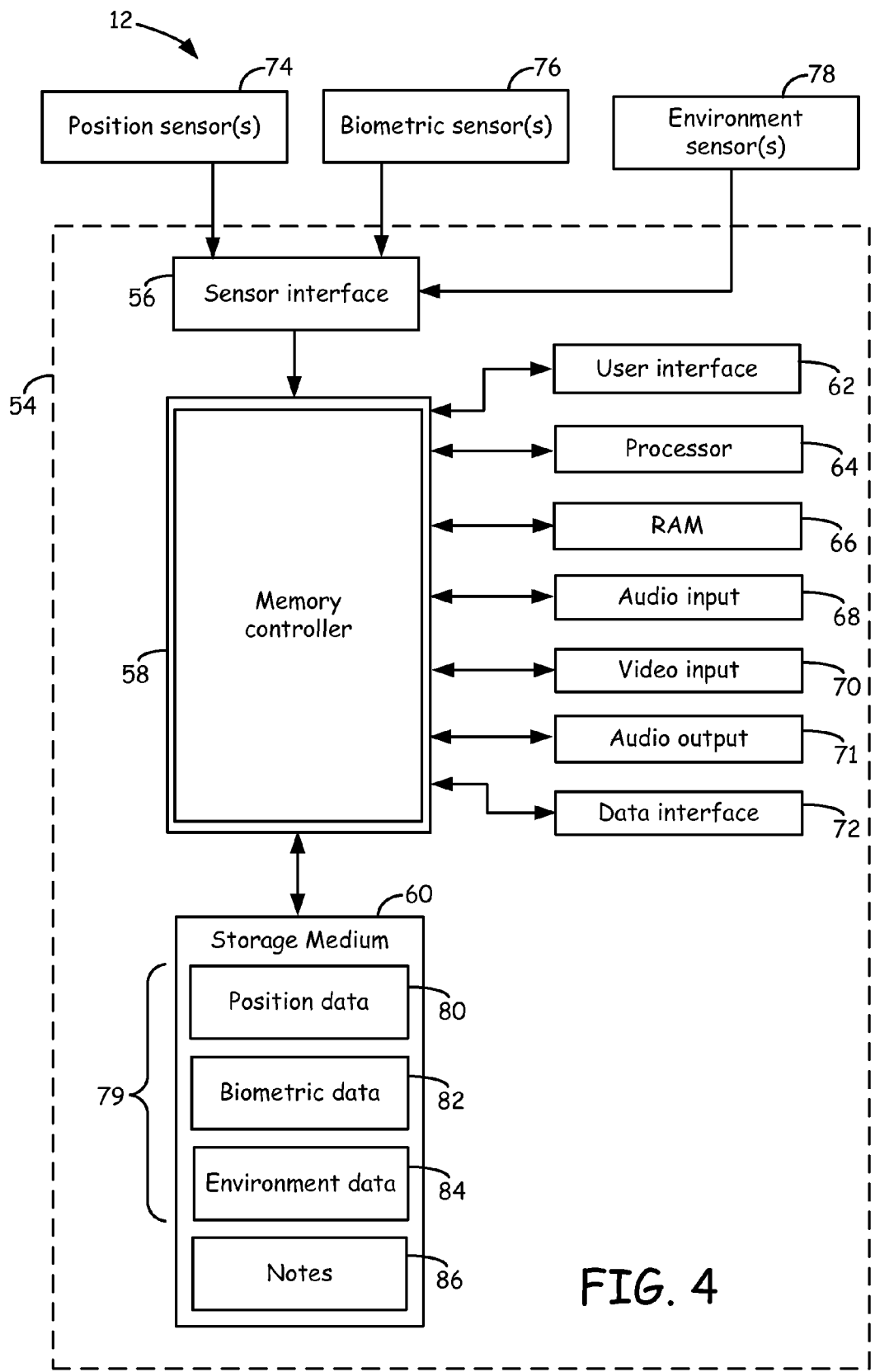
FIG. 4 is a block diagram of an instructor device of the present disclosure.

FIG. 4 illustrates an example embodiment of instructor device 12. Instructor device 12 may be a specialized device that is dedicated for use in recording the workout data and notes pursuant to authoring method 20. Alternatively, instructor device 12 may be a commercially-available product, such as a currently available sports watch, cycling computer, and the like, which is configured with firmware/software to record the workout data and notes pursuant to authoring method 20.

In the shown embodiment, instructor device 12 includes device housing 54, sensor interface 56, memory controller 58, storage medium 60, user interface 62, processor 64, RAM 66, audio input 68, video input 70, audio output 71, and data interface 72. Device housing 54 may be any suitable housing, which preferably allows instructor device 12 to be worn or otherwise retained by instructor 10, such as a wearable watch housing and strap, a cycling computer housing, a mobile media device, and the like. Instructor device 12 may also include a variety of additional components that are typically contained in portable computer-based devices (e.g., batteries, firmware, and the like).

Sensor interface 56 is a device interface for communicating with one or more sensors, such as position sensor(s) 74, biometric sensor(s) 76, and/or environment sensor(s) 78. In one embodiment, sensor interface 56 may be a wireless receiver to communicate with sensors 74, 76, and/or 78 over a wireless connection, such as under a radio-frequency (RF) protocol, a Wi-Fi wireless protocol, or an ANT+ wireless protocol.

Position sensor 74 is one or more sensors or receivers configured to measure route information of the athletic workout, such as GPS waypoint coordinates, elevation, speed, and the like. Examples of suitable devices for position sensor 74 include GPS receivers, which typically provide time-stamped data.

Biometric sensor 76 is one or more sensors or receivers configured measure biometric parameters of instructor 10, such as heart rate, power output, cadence, stride count, core temperature, and the like. Examples of suitable devices for biometric sensor 76 include heart rate monitors, power meters, cadence sensors (e.g., magnet-based and accelerometer-based sensors), pedometers, stride sensors, and ingestible temperature capsules.

Environment sensor 78 is one or more sensors or receivers configured to measure environment information during the athletic workout, such as temperature, humidity, wind speeds, and the like. Examples of suitable devices for environment sensor 78 include electronic temperature sensors, humidity detectors, and pressure gauges.

Memory controller 58 is a circuit assembly that interfaces the components of instructor device 12 with RAM 66, and provides bus clock cycles for time-stamped data recording. Storage medium 60 is one or more computer readable media, such as solid-state media and/or hard disc drives. Storage medium 60 is configured to record the workout data received from sensors 74, 76, and 78, which is collectively referred to as workout data 79. For example, storage medium 60 may store digital data for route information (e.g., position data 80), biometric parameters (e.g., biometric data 82), and environment information (e.g., environment data 84). In alternative embodiments, memory controller 58 may be omitted, and processor 64 may control data transfers (e.g., to storage medium 60 and RAM 66).

User interface 62 is a user display and input interface, allowing instructor 10 to operate instructor device 12. Processor 64 is one or more processing units, and RAM 66 is one or more volatile random access memory modules. While illustrated as being located within device housing, one or more of the components, such as audio input 68, video input 70, and audio output 71 may be located externally from device housing 54. For example, audio input 68 and/or video input 70 may be wireless components configured to communicate with sensor interface 56.

Audio input 68 is an audio receiver and acoustic-to-electric transducer, such as a microphone. Audio input 68 is configured to receive acoustic signals, such as audio notes from instructor 10, and convert the acoustic signals into electrical audio signals. Video input 70 is a video receiver, such as a video camera, for recording video notes from instructor 10. Processor 64 may convert the received audio and video signals into suitable digital data files (e.g., MP4 file format), which may be stored on storage medium 60 as recorded notes 86. In embodiments in which instructor device 12 only includes audio input 68 (i.e., video input 70 is omitted), processor 64 may convert the audio signals into suitable digital data files (e.g., MP3 file format), which may be stored on storage medium 60 as recorded notes 86.

Audio output 71 is an audio transducing component configured to covert electrical signals into acoustic signals for audible listening (e.g., music, audible alerts, and playback of the recorded notes). Data interface 72 is an interface configured to communicate with and/or receive electrical power from computer-based systems (e.g., computer 14), such as a universal serial bus (USB) interface. Alternatively, instructor device 12 may communicate with computer 14 or other computer-based systems wirelessly, such as with sensor interface 56.

While instructor 10 performs an athletic workout with instructor device 12, one or more of sensors 74, 76, and 78 measure their respective data, which is transmitted to sensor interface 56 and recorded on storage medium 60 as position data 80, biometric data 82, and/or environment data 84. For example, when position sensor 74 is a GPS receiver (carried by instructor 10 or integral with instructor device 12), position data 80 may include time-stamped GPS waypoint coordinates of the workout route, elevation data, and the speeds of instructor 10 during the workout.

Similarly, when biometric sensor 76 is a heart rate monitor worn by instructor 10, biometric data 82 may include time-stamped heart rate values (and/or heart rate zones, percentages of maximum heart rate, etc. . . . ) of instructor 10 during the workout. Furthermore, when environment sensor 78 is an ambient temperature sensor (e.g., an electronic thermometer), environment data 84 may include time-stamped temperatures of the environment during the workout. The term "time-stamped" refers to the data being recorded chronologically.

Also during the athletic workout, instructor 10 may record notes with audio input 68 and/or video input 70 (or textual inputs via user interface 62). For example, during a warm up-phase of the athletic workout, if instructor 10 observes that his or her heart rate or speed is too high on a particular segment of the route, instructor 10 may record an audio note such as "Take it easy right now. Slow down. We are warming up." Similarly, when instructor 10 reaches a main phase of the workout, instructor 10 may record audio notes such as "Pick it up. I want your heart rate above your lactate threshold." and "Stay with me. Don't fall behind."

Additionally, if the ambient temperature begins to warm up, instructor 10 may record a third audio note such as "It is getting warm out here. Make sure you stay hydrated." As can be appreciated, a variety of different notes may be recorded, which may vary depending on multiple factors, such as the particular workout being performed (e.g., running versus cycling), the purpose of the workout (e.g., interval workout versus aerobic pace workout), the intended user during playback method 36 (e.g., experienced athlete versus beginner athlete), and the like.

Figure 5:
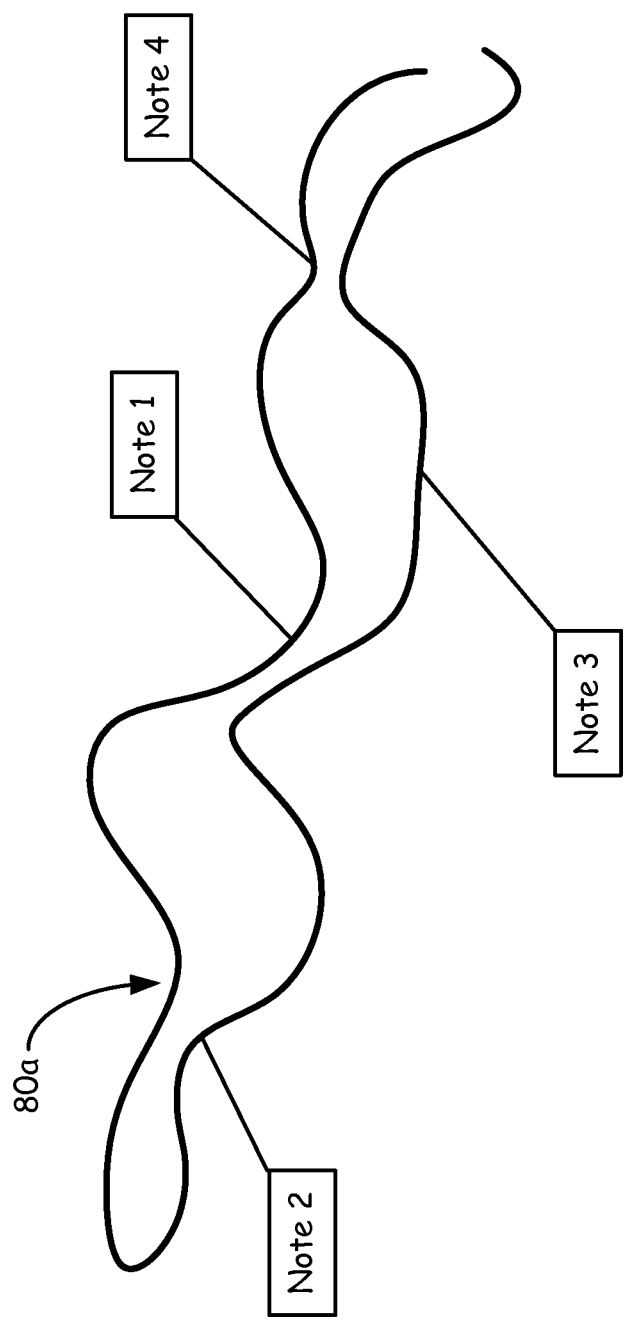
FIG. 5 is a graphical illustration of time-stamped, global positioning system (GPS) coordinate waypoints attained with the instructor device, with linked recorded notes.
Figure 6:
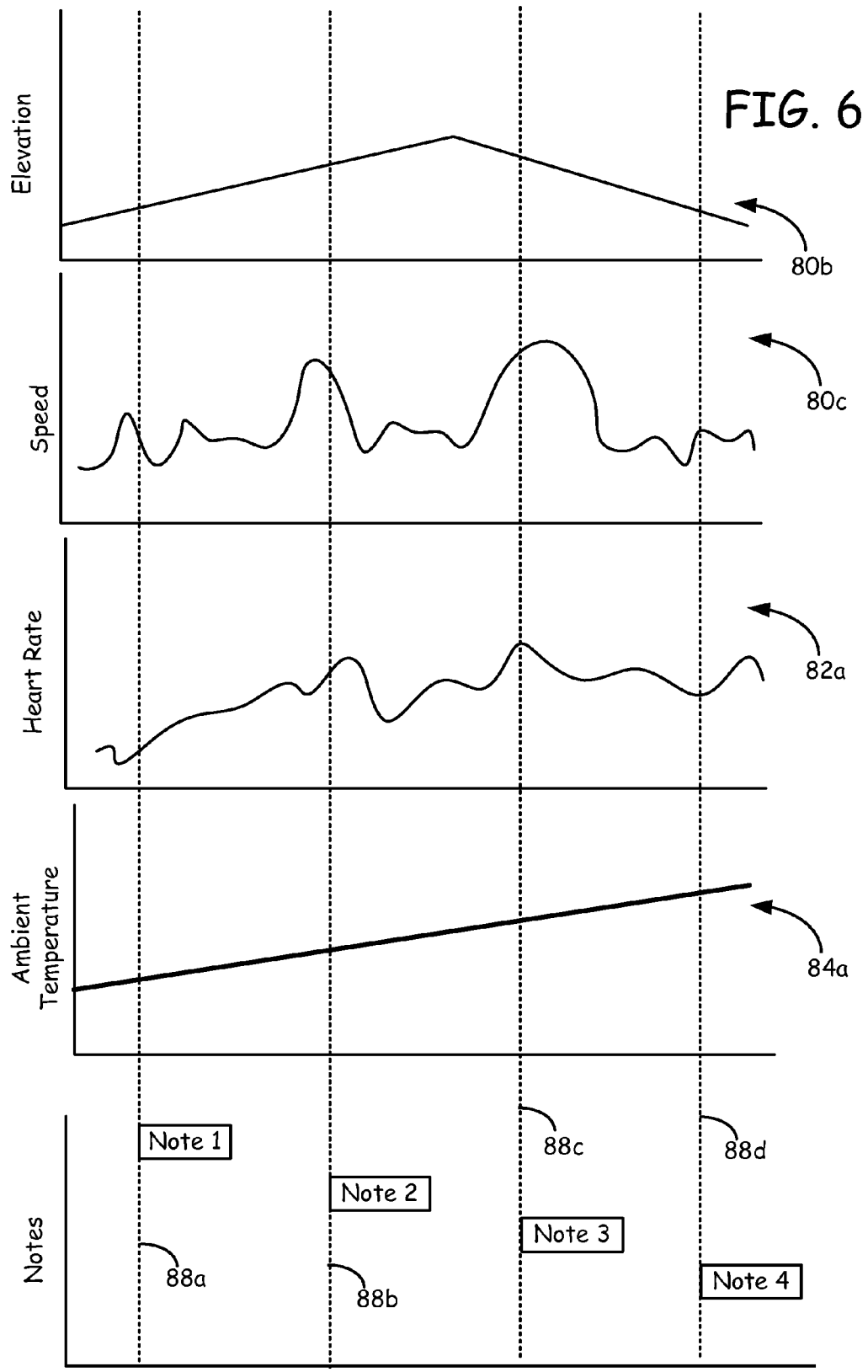
FIG. 6 illustrates plots of additional work out data attained with the instructor device, with linked recorded notes.

As discussed above, each recorded note 86 is desirably linked to workout data 79. For example, each recorded note 86 may have a time stamp that is synchronized with the time stamps of position data 80, biometric data 82, and/or environment data 84. FIGS. 5 and 6 illustrate the time-stamped linking between recorded notes 86 and position data 80, biometric data 82, and/or environment data 84. As shown in FIG. 5, which is a graphical illustration of time-stamped GPS coordinate waypoints 80a (from position data 80), recorded notes 86 may be linked to the GPs coordinate waypoints that were received at the time the given notes 86 were recorded.

FIG. 6 illustrates plots of elevation 80b (from position data 80), speed 80c (from position data 80), heart rate 82a (from biometric data 82), ambient temperature 84a (from environment data 84), and recorded notes 86, each of which have the same time axis. The time-stamp linking between recorded notes 86 and the elevations, speeds, heart rates, and ambient temperatures are indicated by lines 88a-88d. This linking between recorded notes 86 and workout data 79 provides a convenient mechanism for instructor 10 to identify trigger conditions to attach to recorded notes 86. This linking is particularly useful when attaching trigger conditions based on multiple types of workout data (e.g., elevation, heart rate, and ambient temperature).

After completing the athletic workout, instructor 10 may then transfer workout data 79 and recorded notes 86 to computer 14 to attach trigger conditions. In an alternative embodiment, instructor 10 may use instructor device 12 itself to review the workout data and attach the trigger conditions to recorded notes 86. However, in embodiments in which instructor device 12 is a sports watch, it is typically more convenient to use a separate computer-based system (e.g., computer 14) to review the workout data and attach the trigger conditions.

Figure 7:
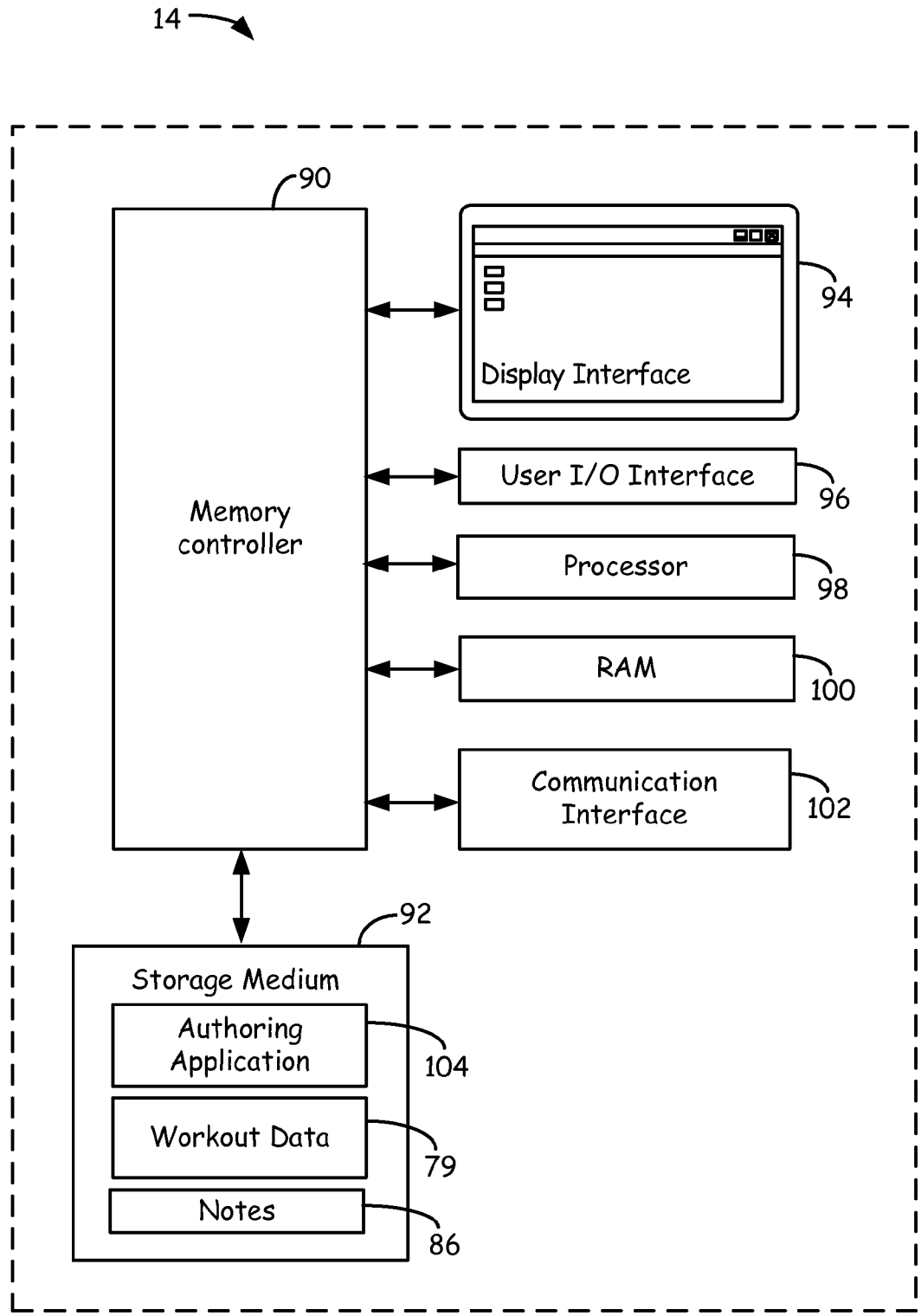
FIG. 7 is a block diagram of a computer-based system for attaching trigger conditions pursuant to the authoring method.

FIG. 7 illustrates an example embodiment of computer 14, which includes memory controller 90, storage medium 92, display interface 94, user input interface 96, processor 98, RAM module 100, and communication interface 102. Computer 14 may also include a variety of additional components that are typically contained in computer-based systems (e.g., BIOS firmware).

Memory controller 90 includes a circuit assembly that interfaces the components of computer 14 with RAM 100. Storage medium 92 includes one or more computer readable media, such as solid-state media and/or hard disc drives, which may be removable or non-removable devices. Storage medium 92 is configured to store workout data 79 and recorded notes 86 transferred from instructor device 12. In addition, storage medium 92 may store authoring application 104, which includes programmable instructions that may be executed with processor 98 for reviewing workout data 79 and attaching trigger conditions to recorded notes 86.

Display interface 94 and user input/output (I/O) interface 96 include user controls (e.g., display monitor, keyboard, and computer mouse), allowing instructor 10 to operate computer 14. In some embodiments, display interface 94 and user I/O interface 96 may be combined in a single interface, such as a touch-screen display. Processor 98 includes one or more processing units, and RAM 100 includes one or more volatile random access memory modules. Communication interface 102 includes an interface configured to communicate with instructor device 12 and athlete device 18, and may also be configured to communicate with other computer-based systems over networks (e.g., over the Internet).

Figure 8:
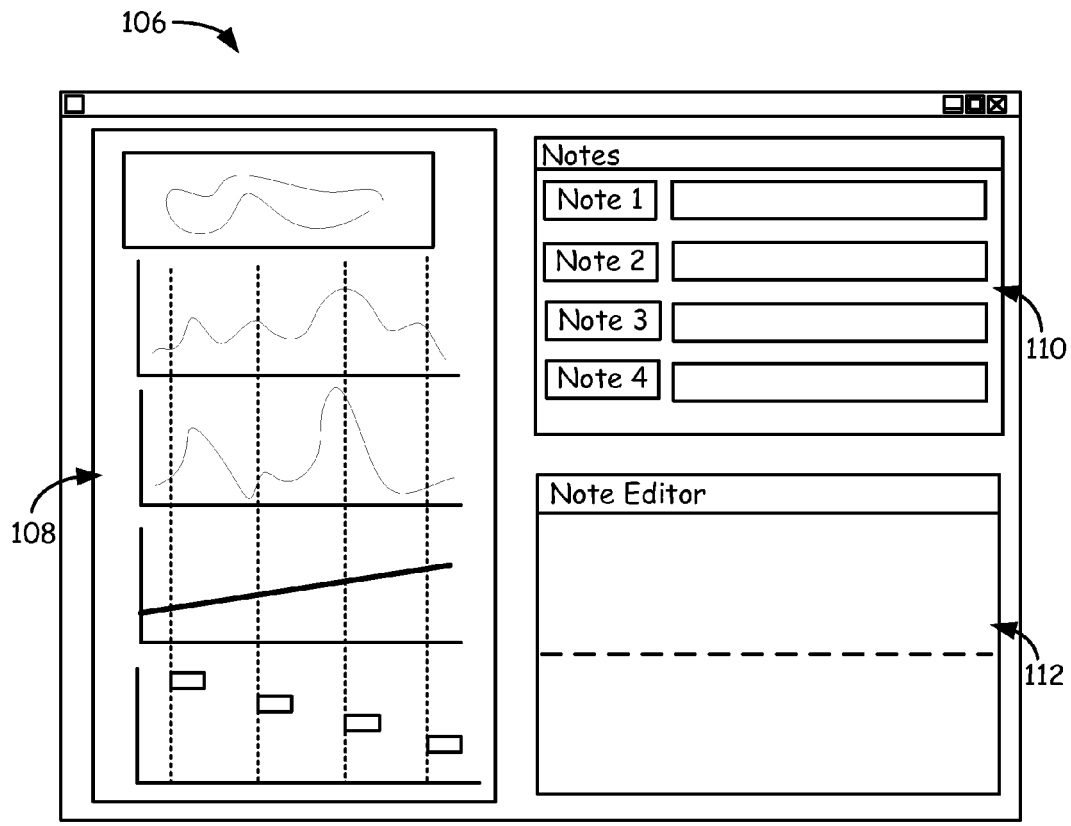
FIG. 8 is an illustration of a screen display of the computer-based system.

FIG. 8 illustrates an example screen 106 presented on display interface 94 after authoring application 94 is loaded by processor 98 and stored in RAM 100. In the shown embodiment, screen 106 includes workout data module 108, notes module 110, and note editor module 112. Workout data module 108 is a suitable section for displaying the linked arrangement of workout data 79 and notes 86. The information in workout data module 108 is desirably selectable to allow instructor 10 to modify portions of the data, such as the time-stamped locations of notes 86. Notes module 110 provides a convenient selectable list of notes 86. When instructor 10 selects one of the notes 86 in notes module 110, information relating to the given note 86 appears in note editor module 112.

Figure 9:
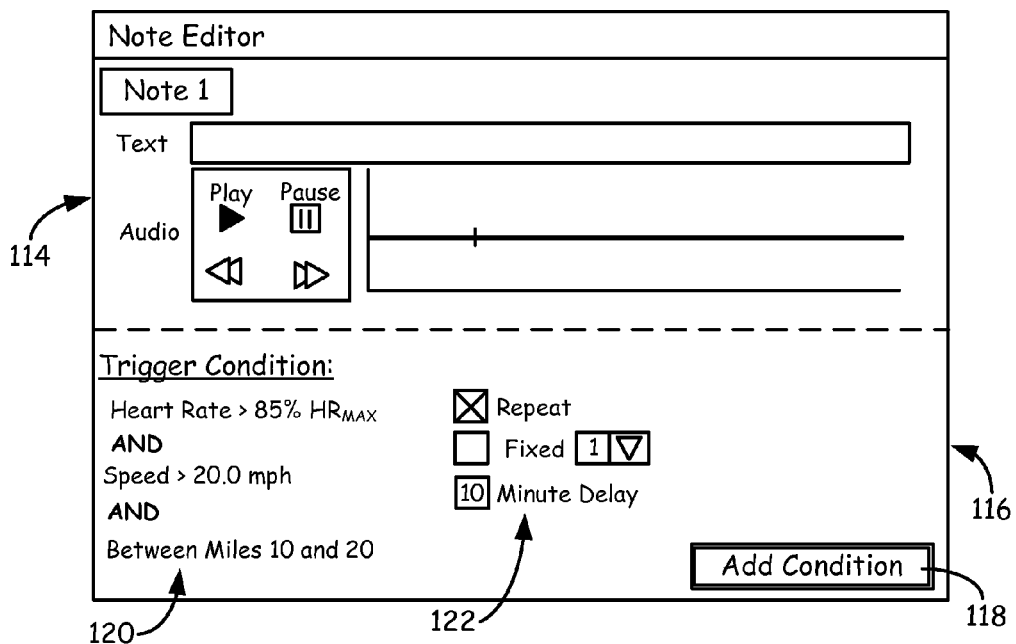
FIG. 9 is an illustration of an example note editor module of the screen display shown in FIG. 8.

FIG. 9 illustrates an example layout for note editor module 112 when a given note 86 is selected. As shown, note editor module 112 includes information section 114 (top portion of note editor module 112) and trigger condition section 116 (bottom portion of note editor module 112). At information section 114, instructor 10 can insert textual information to the selected note 86, and can play a clip of the selected note 86. In some embodiments, note editor module 112 may also include software tools for editing the selected note 86.

At trigger condition section 116, instructor 10 can attach trigger conditions to the selected note 86, such as with button 118. Button 118 may accordingly present a user selectable list of trigger conditions that may be used. Trigger condition section 116 may also include list 120 of the one or more trigger conditions attached to the selected note 86. In the shown example, the trigger conditions that need to be reached before the selected note 86 will play are a heart rate greater than 85% of a maximum heart rate of athlete 16, a speed greater than 20 miles-per-hour, and a location between 10 and 20 miles along the route. In other words, this selected note 86 will only play if athlete device 18 detects that all three of these conditions are simultaneously reached.

Trigger condition section 116 may further include menu 122, which allows instructor 10 to select how many times during the workout that the selected note 86 may be played. For example, menu 122 my include a "repeat" selection box, which designates that the selected note 86 will be played every time the trigger condition shown in list 120 is reached.

Menu 122 may also include a "fixed" selection box having a separate pull-down menu to allow instructor 10 to select how many times the selected note 86 will play during a single athletic workout. Menu 122 may further include a "delay" selection to allow instructor 10 to designate a delay period (e.g., 10 minutes) between when the same selected note 86 may be replayed. This prevents the selected note 86 from being repeatedly played in a continuous manner.

After attaching the trigger conditions to notes 86, instructor 10 may then export workout data 79, notes 86, and the attached trigger conditions as a workout file. The exported workout file may then be stored on computer 14 and/or posted to an e-commerce server for subsequent purchase and download (e.g., by athlete 16). Athlete 16 may then import the workout file to athlete device 18.

Figure 10:
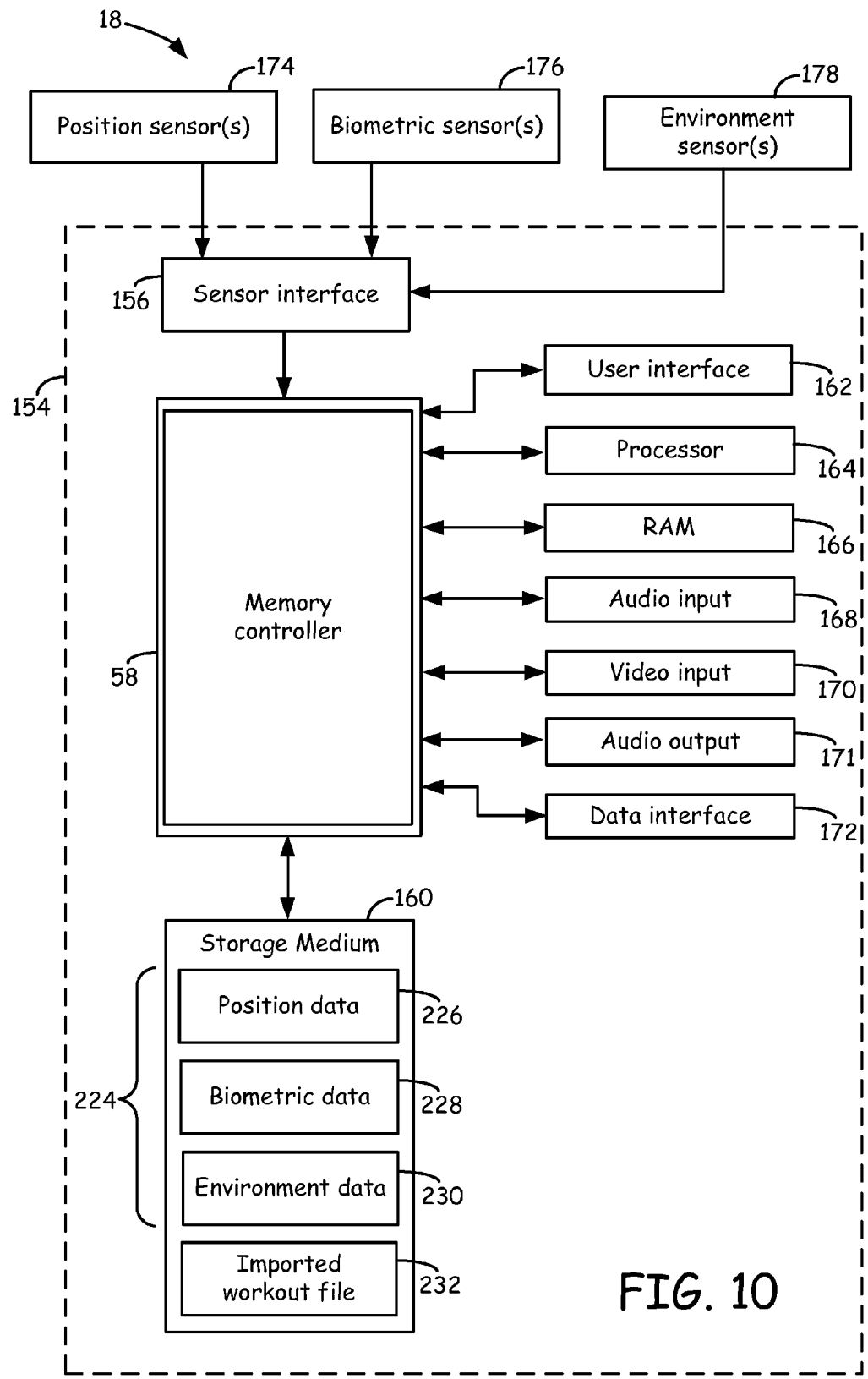
FIG. 10 is a block diagram of an athlete device of the present disclosure.

FIG. 10 illustrates an example embodiment of athlete device 18, which may include the same components as instructor device 12, where the respective references numbers are increased by "100". As discussed above, in some embodiments, instructor device 12 and athlete device 18 may be identical devices, allowing the same type of device to be used for both authoring method 20 and playback method 36. In these embodiments, the user (e.g., instructor 10 or athlete 16) may select the given device to operate under authoring method 20 or playback method 36. In other embodiments, as discussed above, athlete device 18 may be a computer-controlled exercise system (e.g., an indoor training system) configured to operate with workout file 79.

When operating as athlete device 18 under playback method 36, storage medium 160 is configured to record workout data received from sensors 174, 176, and 178 for athlete 16, referred to as workout data 224. For example, storage medium 160 may store position data 226 for athlete 16, biometric data 228 for athlete 16, and environment data 230 for athlete 16. In addition, storage medium 160 retains the imported workout file, referred to as workout file 232.

Athlete 16 may initiate workout file 232 by loading workout file 232 to RAM 166 with processor 164. Athlete 16 may then perform an athletic workout with athlete device 18 that corresponds to workout file 232. While athlete 16 performs the athletic workout, sensors 174, 176, and/or 178 records his or her workout data, which is recorded on storage medium 160. When athlete 16 reaches one or more of the trigger conditions (step 46), the related notes 86 are then played to athlete 16. As discussed above, this can provide a virtual or real-life instructor experience for athlete 16 while athlete 16 performs the athletic workout pursuant to playback method 36.

As can be appreciated, sensors 174, 176, and 178 of athlete device 18 desirably match sensors 74, 76, and 78 of instructor device 12 to maximize the potential use of the trigger conditions. In situations in which one or more of sensors 174, 176, and 178 do not correspond to sensors 74, 76, and 78, athlete device 18 may present display information on user interface 162 to identify which sensors are missing. In some embodiments, athlete device 18 may compensate for sensor differences by removing trigger conditions that otherwise require the missing sensors.

Instructor device 10 and athlete device 18 are suitable devices for generating and use workout data (e.g., workout data 79) pursuant to authoring method 20 and playback method 36. As such, these devices are capable of generating workout files in a convenient and efficient manner, of providing virtual or real-life instructor experiences for subsequent users (e.g., athlete 16).

Although the present disclosure has been described with reference to preferred embodiments, workers skilled in the art will recognize that changes may be made in form and detail without departing from the spirit and scope of the disclosure.

The invention claimed is:

1. A method for generating a workout file, the method comprising:
    performing an athletic workout;
    in a portable computerized instructor device, recording workout data while performing the athletic workout, the recorded workout data being selected from the group consisting of route information of the athletic workout, biometric parameters, environment information during the athletic workout, and combinations thereof;
    recording notes in the portable computerized instructor device while performing the athletic workout, the recorded notes being linked to the recorded workout data;
    storing the recorded workout data and the recorded notes on a non-transitory computer readable medium;
    attaching trigger conditions to the stored notes via the portable computerized instructor device; and
    exporting the stored workout data, the stored notes, and the attached trigger conditions from the portable computerized instructor device as the workout file, wherein the exported workout file is configured to be used by a subsequent user to repeat the athletic workout using a portable computerized athlete device in a manner that plays the notes when the subsequent user performs the trigger conditions.

2. The method of claim 1, wherein recording the notes while performing the workout comprises recording audio notes.

3. The method of claim 1, wherein the route data comprises time-stamped GPS coordinate waypoints defining a route for the athletic workout.

4. The method of claim 1, wherein at least one of the attached trigger conditions comprises a biometric parameter trigger condition.

5. The method of claim 1, wherein two or more of the attached trigger conditions are attached to one of the recorded notes.

6. The method of claim 1, wherein recording the workout data comprises recording the workout data with a wearable electronic device.

7. The method of claim 6, wherein the portable computerized instructor device and the portable computerized athlete device comprise the same device.

8. The method of claim 6, and further comprising transferring the recorded workout data from the wearable electronic device to a computer-based system, wherein the non-transitory computer readable medium is a component of the computer-based system, and wherein attaching the trigger conditions to the stored notes and exporting the stored workout data are performed with the computer-based system.

9. A method for generating a workout file, the method comprising:
performing an athletic workout along a route;
recording in a portable computerized instructor device GPS coordinate waypoints along the route while performing the athletic workout with a GPS receiver;
recording notes in the portable computerized instructor device while performing the athletic workout along the route, wherein the notes are linked to the recorded GPS coordinate waypoints corresponding to when the notes are recorded;
storing the recorded GPS coordinate waypoints and the recorded notes on a non-transitory computer readable medium;
attaching trigger conditions to the recorded notes via the portable computerized instructor device, wherein at least a portion of the attached trigger conditions are based on the GPS coordinate waypoints; and
exporting the GPS coordinate waypoints, the recorded notes, and the attached trigger conditions from the portable computerized instructor device as the workout file.

10. The method of claim 9, wherein performing the athletic workout along the route, recording the GPS coordinate waypoints along the route, and recording the notes are each performed by a first person, and wherein the method further comprises recording biometric parameters of the first person while performing the athletic workout, wherein the recorded notes are also time-stamp linked to the biometric parameters of the first person corresponding to when the notes are recorded.

11. The method of claim 10, wherein at a second portion of the attached trigger conditions are based on biometric parameters.

12. The method of claim 9, and further comprising recording environment data while performing the athletic workout, wherein the recorded notes are also time-stamp linked to the environment data corresponding to when the notes are recorded.

13. The method of claim 12, wherein at a second portion of the attached trigger conditions are based on environment information.

14. The method of claim 9, wherein recording the GPS coordinate waypoints and recording the notes are each performed with a wearable electronic device, and wherein storing the recorded GPS coordinate waypoints and the recorded notes, attaching the trigger conditions, and exporting the GPS coordinate waypoints, the recorded notes, and the attached trigger conditions are each performed with a computer-based system having the non-transitory computer readable medium.

15. A workout device assembly comprising:
one or more sensors coupled to a portable computerized instructor device and configured to read workout data while a first person performs an athletic workout, the workout data being selected from the group consisting of route information of the athletic workout, biometric parameters of the first person, environment information during the athletic workout, and combinations thereof;
one or more note inputs in the portable computerized instructor device configured to receive notes from the first person while the first person performs the athletic workout;
the portable computerized instructor device configured to transmit the recorded workout data and the recorded notes; and
a non-transitory computer readable medium retaining programmable instructions that, when executed with a computer processor in the portable computerized instructor device, enable trigger conditions to be attached the recorded notes, and exportation of the recorded workout data, the recorded notes, and the attached trigger conditions as a workout file.

16. The workout device assembly of claim 15, wherein the one or more sensors comprise a GPS receiver.

17. The workout device assembly of claim 15, wherein the first device comprises a portable electronic device that is wearable by the first person.

18. The workout device assembly of claim 17, and further comprising a computer-based system, wherein the non-transitory computer readable medium and the computer processor are components of the computer-based system.

19. The workout device assembly of claim 15, wherein the one or more note inputs comprise an audio input.

20. The workout device assembly of claim 15, and further comprising a second device transportable by a second person, and configured to operably receive and execute the workout file, the second device being configured to receive workout data from the second person, and to play the recorded notes of the workout file when received workout data from the second person reaches at least one of the attached trigger conditions of the workout file.

* * * * *